United States Patent
Chang

[19]

[11] Patent Number: 5,830,189

[45] Date of Patent: Nov. 3, 1998

[54] CATHETER HUB TO NOSE ENGAGEMENT

[75] Inventor: Joseph J. Chang, Avon, Conn.

[73] Assignee: Johnson & Johnson Medical, Inc., Arlington, Tex.

[21] Appl. No.: 482,591

[22] Filed: Jun. 7, 1995

[51] Int. Cl.⁶ .................................................. A61M 5/178
[52] U.S. Cl. ...................... 604/164; 604/171; 604/264; 604/283
[58] Field of Search .................................. 604/164, 165, 604/166, 170, 171, 283, 167

[56] References Cited

U.S. PATENT DOCUMENTS

| | | | |
|---|---|---|---|
| 2,704,074 | 3/1955 | Butler . | |
| 4,239,042 | 12/1980 | Asai | 604/164 |
| 4,547,194 | 10/1985 | Modrehead | 604/283 |
| 4,781,703 | 11/1988 | Walker | 604/283 |
| 4,904,246 | 2/1990 | Atkinson | 604/167 |
| 4,921,479 | 5/1990 | Grayzel | 604/164 |
| 4,944,725 | 7/1990 | McDonald . | |
| 5,064,416 | 11/1991 | Newgard | 604/167 |
| 5,080,654 | 1/1992 | Picha | 604/167 |
| 5,125,904 | 6/1992 | Lee | 604/164 |
| 5,135,504 | 8/1992 | McLees | 604/164 |
| 5,312,371 | 5/1994 | Dombrowski et al. . | |

*Primary Examiner*—Wynn Wood Coggins
*Assistant Examiner*—Jennifer R. Sadula
*Attorney, Agent, or Firm*—Joseph F. Shirtz

[57] ABSTRACT

A catheter hub to nose engagement for securely engaging the hub of a catheter to the nose of a catheter emplacement unit is described. The attachment mechanism may be as simple as an elastic tube which provides an interference fit between the catheter hub and the nose of the emplacement unit. In an alternate embodiment the nose has a longitudinal slot to provide a split nose tip. The split nose tip is held in a separated position by the passage of a cannula therethrough and an enlarged burr end securely engages the hub and nose together. In another embodiment the nose has a longitudinally tapered nose tip and the tapered nose tip has an enlarged burr end to securely engage the hub and nose together. In a further embodiment the nose has an internal undercut in which an elastic plug is secured which is positioned between the catheter hub and nose. The elastic plus has a through hole having a diameter slightly smaller than the diameter of a catheter needle such that when the needle is inserted into the through hole the outer diameter of the elastic plug is expanded.

13 Claims, 3 Drawing Sheets

CATHETER HUB TO NOSE ENGAGEMENT

BACKGROUND OF THE INVENTION

1. Field of the Invention

The present invention relates to clinical apparatus of the type in which pointed needles are used to puncture the skin of a patient, and in particular to catheters employing such needles to effectuate venous punctures.

The present invention relates generally to a catheter hub to nose engagement, and more particularly pertains to a catheter hub to nose engagement in which a catheter hub and nose are secured together for a) providing a hermetic seal therebetween to prevent blood leakage and b) securing the catheter hub and nose fixedly together as one integral unit during threading of the catheter. However, for separation of the catheter, the hub/nose becomes relatively loose so that the clinician can easily separate the locked hub introducer needle assembly from the hub by a simple straight pulling or twist-pulling action. The design approach results in looser requirements for the dimensional tolerances of the hub internal diameter and the nose outside diameter, and also provides a more consistent and secure hub/nose engagement.

2. Discussion of the Prior Art

It is well known and common practice by physicians to inject fluids and drugs directly into the bloodstream of patients. Also, during surgical operations, it is frequently necessary to administer whole blood transfusions and parenteral fluids. Historically, introduction of such fluids into the cardiovascular system of a patient has required the making of a venipuncture using a hollow rigid needle having a proximal attachment site for fluid connecting the needle to a source of intravenous fluid or the like. This method of administering fluids created some persisting problems in the art. Primarily, the rigidity of the needle within the vein requires that the needle, usually on the arm, be maintained, for reasons of safety, in a fixed position at the general site of the venipuncture throughout the duration of fluid administration or transfusion, which may consume considerable time. Secondly, where it has been necessary to periodically draw blood samples and/or successively administer intravenous fluids, the patients may be required to experience a venipuncture each time, which repeated venipunctures are generally highly traumatic.

More recently it has been the practice to insert a flexible catheter tube into a vein and leave the catheter tube in such a position for purposes such as periodically administering fluids, transfusions and medication, collecting of blood samples, etc. In this way, the trauma, extravasation, infiltration, etc., of repeated venipunctures are avoided and the danger and discomfort of leaving a rigid needle in the body for a prolonged period of time are overcome. To place the distal end of such a flexible catheter tube within a body cavity, such as a vascular cavity, a cannulated or hollow needle is used to make the venipuncture. Thereafter following the venipuncture, the catheter tube, which is telescopically mounted with respect to the needle, is displaced relative to the needle into the vein of the patient. The needle may thereafter be completely removed from the catheter tube and disposed of.

Intravenous catheters for the infusion of fluids into the peripheral vein of a patient are frequently produced in two general forms: through-the-needle catheters, in which a catheter is threaded through the needle cannula and into the vein of a patient, and over-the-needle catheters, in which the needle and a concentric outer catheter are inserted into the vein, and the needle is then withdrawn from the emplaced catheter.

McDonald U.S. Pat. No. 4,944,725 discloses a catheter which is relative to some embodiments of the present invention by disclosing a catheter in which insertion of a needle into the catheter causes the catheter nose to be locked relative to the catheter hub. McDonald discloses two different embodiments of such a locking mechanism. In a first embodiment, a locking tongue is defined by a U-shaped opening formed in the wall of the hub near the forward end thereof. A tongue is connected at its rear end to the wall of the hub, and is resiliently biased to extend slightly radially inwardly. A boss is located on the inner side of the locking tongue. When the needle is inserted into the catheter it presses against the boss, causing the locking tongue to be pushed radially outwardly into the recess of the catheter fitting. The housing is thus locked to the catheter fitting. When the needle is withdrawn rearwardly, the rearward displacement of the needle provides clearance which allows the locking tongue to spring radially inwardly, and thus disengage from the catheter fitting. The housing is then unlocked from the catheter fitting. In the second embodiment, two free-standing resilient locking tongues are defined by two oppositely disposed U-shaped openings formed in the wall of the hub near the forward end thereof. Each locking tongue has a boss located on its radially outer side, and has a flex point at its rearward end where it is integrally joined to the hub. The bosses of the locking tongues perform the locking function by cooperating with an annular recess formed on the internal wall of the catheter fitting. As the needle is pushed into the catheter, the bosses of the locking tongues are engaged within the recess of the catheter fitting so that the housing is locked to the catheter fitting. Withdrawal of the needle allows radially inward flexure of the locking tongues out of the recess. The housing is therefore unlocked and can be separated from the catheter fitting.

A current prior art design for a catheter (PROTECTIV™ IVC) provides a simple interference fit between a hub and a nose for a) providing a hermetic seal therebetween to prevent blood leakage and b) securing the hub and nose fixedly together as one unit during threading and locking of a catheter. This approach requires tight dimensional tolerances for the hub internal diameter and also for the nose outside diameter.

SUMMARY OF THE INVENTION

Accordingly, it is a primary object of the present invention to provide an improved catheter hub to nose engagement.

A further object of the subject invention is the provision of an optimized hub/nose engagement which functions so that the hub and nose are secured together as one integral unit during threading of the catheter. However, for separation of the catheter, the hub/nose becomes relatively loose so that the clinician can easily separate the locked Plastic Hub Introducer Needle (PHIN) assembly from the hub by a simple straight pulling action.

In accordance with the teachings herein, the present invention provides a catheter comprising a catheter hub and nose in which an elastic tube is provided between the catheter hub and nose. The hub and nose are securely engaged together by an interference fit between the hub and nose and also by an interference fit between the elastic tube and the nose.

In greater detail, the nose is provided with an internal undercut in which a nose extender is secured, and the nose extender is securely engaged within the elastic tube. In a second embodiment, the nose has a longitudinal slot to provide a split nose tip, and the split nose tip has an enlarged burred end to securely engage the hub and nose together. This second embodiment is preferably utilized in combination with an elastic tube as described, or can be used also without such an elastic tube. In another embodiment, the nose has a longitudinally tapered nose tip, and the tapered nose tip has an enlarged burred end to securely engage the hub and nose together. In a further embodiment, the nose has an internal undercut in which an elastic plug is secured which is positioned between the catheter hub and nose. The elastic plug has a through hole having a diameter slightly smaller than the diameter of the catheter needle, such that when the needle is inserted into the through hole, the outer diameter of the elastic plug is expanded thereby, such that the hub and nose are securely engaged together by an interference fit between the hub and the elastic plug.

BRIEF DESCRIPTION OF THE DRAWINGS

The foregoing objects and advantages of the present invention for a catheter hub to nose engagement may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
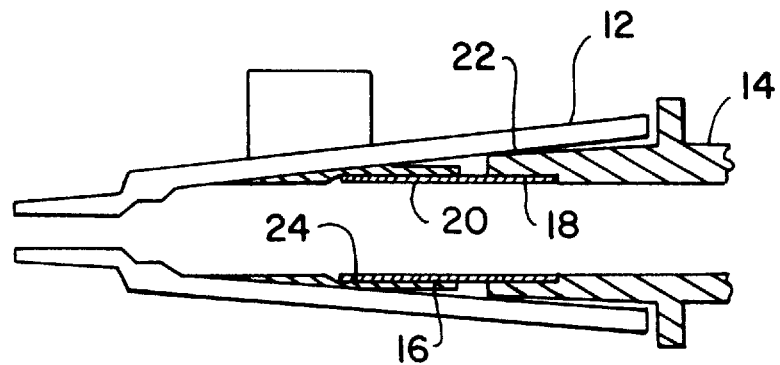
FIG. 1 illustrates a first embodiment of a catheter hub to nose engagement pursuant to the teachings of the present invention wherein a catheter hub and nose are secured together with the assistance of an elastic pliable tube which is positioned between the hub and a nose extender.
Figure 2:
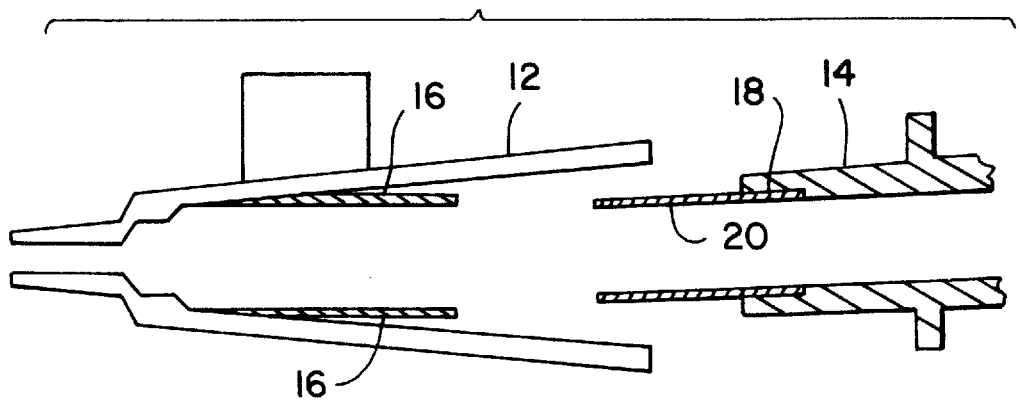
FIG. 2 illustrates the embodiment of FIG. 1 in a nonengaged position.
Figure 3:
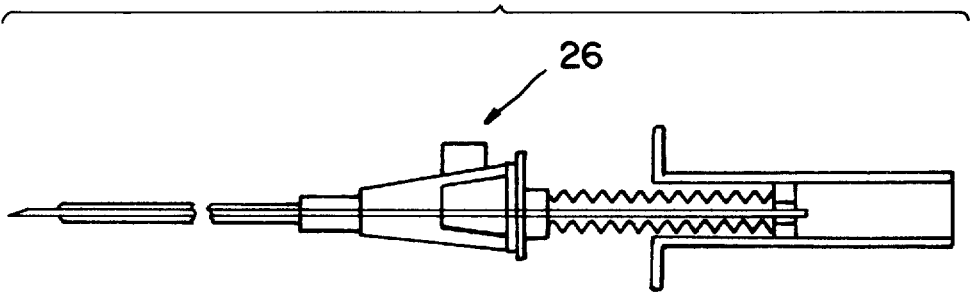
FIG. 3 illustrates the embodiment of FIGS. 1 and 2 with a needle inserted therethrough during threading of the catheter.

Referring to the drawings in detail, FIG. 1 illustrates a first embodiment of a catheter hub to nose engagement pursuant to the teachings of the present invention wherein a catheter hub and nose are secured together with the assistance of an elastic pliable tube which is positioned between the hub and a nose extender. FIG. 2 illustrates the embodiment of FIG. 1 in a nonengaged position, and FIG. 3 illustrates the same embodiment with a needle inserted therethrough during threading of the catheter. In this embodiment, a hub 12 and a nose 14 are secured together for a) providing a hermetic seal therebetween to prevent blood leakage and b) securing the hub 12 and nose 14 fixedly together as one integral unit during threading of a catheter.

In the design of the present invention, a soft pliable plastic or rubber, such as a Silastic™, tube 16 is placed on the tip of the nose or inserted inside the hub 12. This approach results in looser requirements for the dimensional tolerances and also provides a more consistent and secure hub/nose engagement.

The nose 14 has an internal undercut at 18 to secure a nose extender 20 to the end thereof. A flexible elastic pliable tube 16 is positioned with an interference fit within the hub 12, and during engagement of the hub 12 to the nose 14, as illustrated in FIG. 1, an interference fit is provided at two locations: the hub/nose at 22 and the nose extender/elastic tube at 24. This arrangement provides a tighter and more consistent hub/nose interference fit so that the catheter can be threaded by pushing the sideport 26 of the assembly while the nose 14 is securely connected with the hub 12, as illustrated in FIGS. 1 and 3.

Figure 4:
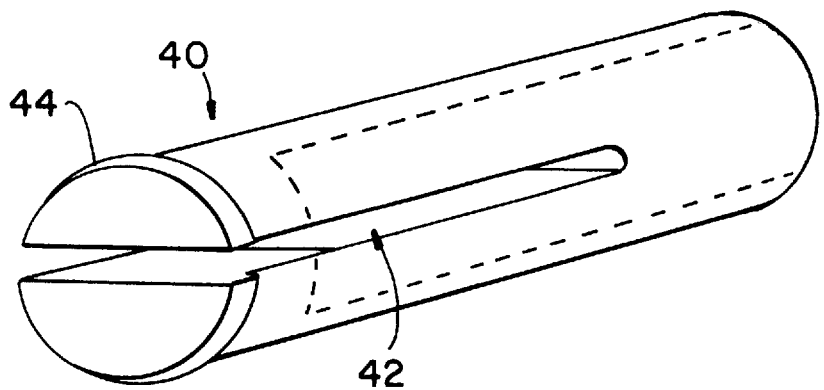
FIGS. 4 and 5 are respectively sectional and perspective views of a catheter split nose having a burred nose tip.
Figure 5:
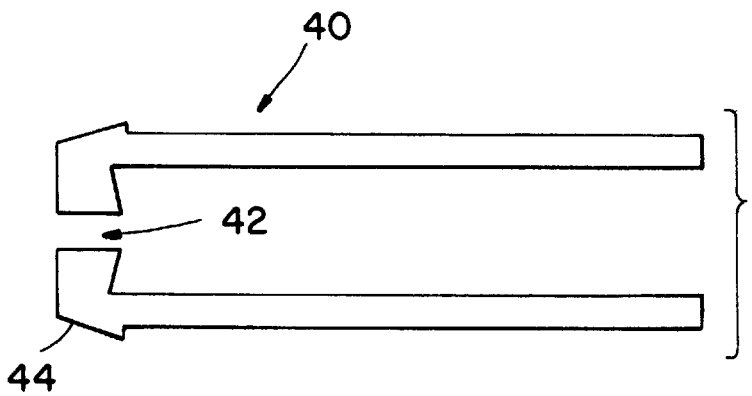

FIGS. 4 and 5 illustrate respectively sectional and perspective views of a slightly more complicated design provided with a split nose 40, provided by a longitudinal slot 42, and also having a burred tip end 44. This second embodiment is preferably utilized in combination with an elastic tube as described, or can be used also without such an elastic tube. Similar to the concept of the McDonald patent, the insertion of a needle shaft therethrough causes the split nose 40 to be tightly engaged with a catheter hub. When the needle shaft is withdrawn, the engagement force is greatly reduced since the nose is cleared of the elastic tube 16. Compared with the McDonald concept, a major difference is that no undercut is required at the hub interior. The elastic tube 16 and the burred tip 44 are tightly secured together to provide the required hub/nose interference engagement force.

Figure 6:
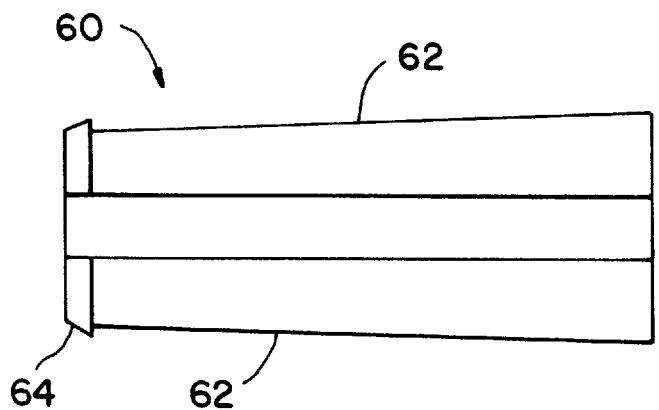
FIG. 6 illustrates a further embodiment of the present invention having a tapered nose with a burred nose tip.

FIG. 6 illustrates a further embodiment 60 of the present invention having a tapered nose 62 with a burred tip 64. The interference fit between the tapered nose 62 and the elastic tube 16, along with the securement action provided by the burred tip 64, provides a secure engagement between the hub and the nose.

Figure 7:
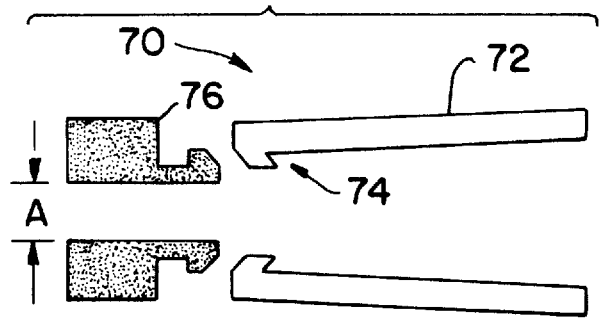
FIG. 7 illustrates a further embodiment of the present invention wherein the tip of a catheter nose is provided with an internal undercut which lockingly engages an elastic plug.

FIG. 7 illustrates a further embodiment 70 of the present invention wherein the tip of a catheter nose 72 is provided with an internal undercut 74 which lockingly engages an elastic plug 76.

Figure 8:
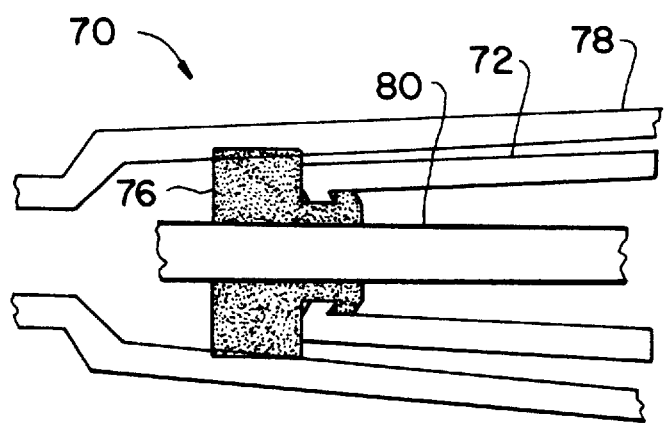
FIG. 8 illustrates the embodiment of FIG. 7 in an engaged position wherein the elastic plug on the catheter nose tip provides an interference engagement fit within a catheter hub.

FIG. 8 illustrates the embodiment 70 of FIG. 7 in an engaged position wherein the elastic plug 76 on the catheter nose 72 tip provides an interference engagement fit within the catheter hub 78.

In the embodiment of FIGS. 7 and 8, the nose section 72 is modified to accept an elastic plug 76. The plug 76 is made of low modulus, and preferably, elastic material. Referring to FIG. 7, the diameter A is slightly smaller than the needle 80 OD (outside diameter) so that when the needle 80 is inserted into the plug A section, the OD of the plug 76 (diameter B) is expanded to be slightly larger than the hub 78 inside diameter, as illustrated by FIG. 8. Therefore, an interference force exists between the elastic plug and the hub interior. This force can be optimized by controlling the plug length (e.g. 0.1") and the through-hole diameter. One obvious benefit of this design is that the elastic plug makes the interference fit more forgiving. It no longer relies upon tight dimensional tolerances between the rigid nose and the hub to provide an interference fit. After the needle 80 is removed from the diameter A section, the plug 76 returns to its original outside diameter (which may be the same or smaller than the hub ID). This provides for an easy separation of the locked device from the hub.

It should be noted here that the A diameter returns to its original dimension when the needle is withdrawn from the A diameter section. This smaller diameter helps to retard blood backflow into the nose. This situation is especially obvious for a small gauge catheter, e.g., 22 gauge and smaller size catheters and needles in which the resulting A diameter is almost zero, which thus allows no blood flow through the plug section.

While several embodiments and variations of the present invention for a catheter hub to nose engagement are described in detail herein, it should be apparent that the disclosure and teachings of the present invention will suggest many alternative designs to those skilled in the art.

What is claimed is:

1. A catheter unit comprising:
   a. a catheter having a hub and catheter emplacement assembly having a nose and a cannula extending slidably through said nose;
   b. an elastic tube provided between the catheter hub and said nose, wherein the hub and nose are securely engaged together by an interference fit between the hub and nose and also by an interference fit between the elastic tube and the nose until said cannula is moved to a position to be withdrawn from said nose.

2. A catheter as claimed in claim 1, wherein the nose is provided with a nose extender which is securely engaged within the elastic tube.

3. A catheter as claimed in claim 1, wherein the nose has a longitudinal slot to provide a split nose tip.

4. A catheter as claimed in claim 3, wherein the split nose tip has an enlarged burred end to securely engage the hub and nose together.

5. A catheter as claimed in claim 1, wherein the nose has a longitudinally tapered nose tip.

6. A catheter as claimed in claim 5, wherein the tapered nose tip has an enlarged burred end to securely engage the hub and nose together.

7. A catheter unit comprising:
   a. a catheter having a hub;
   b. a catheter emplacement unit received within said catheter having a nose having a longitudinal slot to provide a split nose tip which engages an inner surface of said hub.

8. A catheter as claimed in claim 7, wherein the split nose tip has an enlarged burred end to securely engage the hub and nose together.

9. A catheter unit comprising a catheter having a hub and catheter emplacement assembly having a nose and a cannula extending slidably through said nose; an elastic tube provided between the catheter hub and said nose, wherein the hub and nose are securely engaged together by an interference fit between the hub and nose and also by an interference fit between the elastic tube and the nose until said cannula is moved to a position to be withdrawn from said nose; wherein the nose is provided with a nose extender which is securely engaged within the elastic tube and further wherein the nose has an internal undercut in which the nose extender is secured.

10. A catheter comprising;
    a. a catheter hub having an internal diameter, a guard having a catheter nose, and a catheter needle;
    b. an elastic plug provided on said guard between the catheter hub and nose, with the elastic plug having a through hole having a diameter slightly smaller than the diameter of the catheter needle, such that when the needle is inserted into the through hole, the outer diameter of the elastic plug is expanded thereby, to securely engage the hub and nose together by an interference fit between the hub and the elastic plug.

11. A catheter as claimed in claim 10, wherein the nose has an internal undercut in which the elastic plug is secured.

12. A catheter as claimed in claim 10, wherein after the needle is withdrawn from the elastic plug through hole, the elastic plug through hole effectively closes to prevent blood from flowing through the elastic plug through hole.

13. A catheter as claimed in claim 12, wherein the needle gauge is 22 gauge or smaller.

* * * * *